United States Patent [19]
Sellstedt

[11] 4,072,676
[45] Feb. 7, 1978

[54] PROCESS FOR PREPARATION OF 6-AMINOPENICILLANIC ACID DERIVATIVES

[75] Inventor: John H. Sellstedt, Pottstown, Pa.

[73] Assignee: American Home Products Corporation, New York, N.Y.

[21] Appl. No.: 442,954

[22] Filed: Feb. 15, 1974

[51] Int. Cl.² ............................................ C07D 499/04
[52] U.S. Cl. .......................... 260/239.1; 260/306.7 C; 424/271
[58] Field of Search ........................... 260/239.1, 306.7

[56] References Cited
U.S. PATENT DOCUMENTS
3,809,699   5/1974   Ishimaru ........................... 260/306.7

Primary Examiner—Nicholas S. Rizzo

[57] ABSTRACT

A process for the preparation of 6-aminopenicillanic acid is described which comprises reacting a natural penicillin with a phosphorus halide to protect the carboxyl group of the natural penicillin and thereafter reacting the protected penicillin with an acid halide to form the corresponding penicillin imino halide, reacting the imino halide with an alcohol to form an imino ether and subsequent hydrolysis or alcoholysis to 6-aminopenicillanic acid.

5 Claims, No Drawings

PROCESS FOR PREPARATION OF 6-AMINOPENICILLANIC ACID DERIVATIVES

The novel process of the present invention for the preparation of 6-aminopenicillanic acid (hereinafter "6-APA") comprises forming a carboxylic acid protecting derivative of a natural 6-acylaminopenicillanic acid by reacting a trivalent or pentavalent phosphorus halide, with a 6-acylaminopenicillanic acid, reacting the formed anhydride compound with an acid halide to form an imino halide compound and reacting this compound with an alcohol to introduce an ether group on the imino carbon and reforming the free carboxylic acid group and splitting the imino bond to form 6-APA.

The process of this invention may be represented by the following scheme:

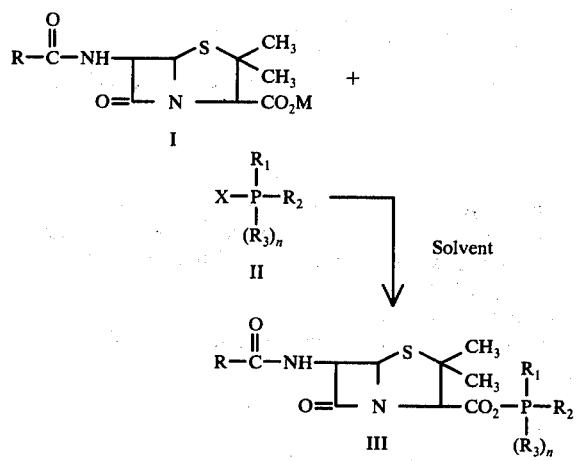

The protected penicillin of formula III may be converted to 6-APA in accordance with the procedure described in South African patent 672,927, the disclosure of which is incorporated herein by reference.

For the compound of formula I any penicillin can be used. As a practical matter, penicillins are used which can be obtained by microbiological processes such as those penicillins wherein R is selected from the class consisting of a lower aliphatic radical having up to and including seven carbon atoms, aryl(lower)alkyl, aryloxy(lower)alkyl, substituted aryl(lower)alkyl and substituted aryloxy(lower)alkyl. Specific illustrations of R as an aliphatic radical include methyl, propyl, 2-pentenyl (penicillin F), n-heptyl (penicillin K), and n-amyl(dihydro penicillin F). The terms aryl(lower)alkyl are illustrated by benzyl (penicillin G), p-hydroxybenzyl (penicillin X), p-aminobenzyl (penicillin T), etc. The term aryloxy(lower)alkyl is illustrated by phenoxymethyl (penicillin V).

In formula I, M is hydrogen or a metal salt (e.g. Na, K), or a tertiary amine (e.g. triethylamine, dimethylaniline, etc.).

The phosphorus halides of formula II are defined as follows: $R_1$ and/or $R_2$ are selected from the class consisting of a (lower)alkoxy radical, aryloxy radical, aryl(lower)alkyloxy radical and halogen; and $R_1$ and $R_2$ may be joined together to form the ring

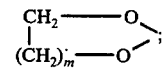

$R_3$ is oxygen (=O); $n$ is a number which is either 0 or 1; $m$ is a number from 0 to 6, X is a halogen atom.

The term "halogen" as used herein means chlorine, bromine, iodine and fluorine. The term "(lower)alkoxy" means a straight chain or branch chain hydrocarbon radical having $C_1$ to $C_7$ carbons as illustrated by methoxy, ethoxy, propoxy, pentoxy, isobutoxy, etc. The term "an aryloxy radical" is illustrated by phenoxy, naphthoxy and substituted derivatives thereof. The term "aryl(lower)alkoxy" is illustrated by benzyloxy, phenethyloxy, etc.

Illustrative of specific compounds falling within the scope of formula II are phosphorus oxychloride, phosphorus trichloride, diphenyl chlorophosphate, diethyl chlorophosphate, phenyl dichlorophosphate, ethyl dichlorophosphate, ethylene chlorophosphate, diethyl chlorophosphite, ethyl dichlorophosphite, ethylene chlorophosphite.

The reaction of a compound of formula I with a compound of formula II is preferably carried out in an anhydrous inert, aprotic solvent. Illustrative of suitable solvents are chloroform, methylene chloride, dichloroethane, tetrahydrofuran, etc. The process of protecting the carboxyl group is carried out at a temperature in the range of about $-40$ to about $+10°$ C., preferably $-10°$ to $+10°$ C., and the molar ratio of a compound of formula I to a compound of formula II is about 0.5:1 to 3:1, preferably about 1:1.

The compounds of formula III are converted to 6-APA in accordance with the following reaction scheme:

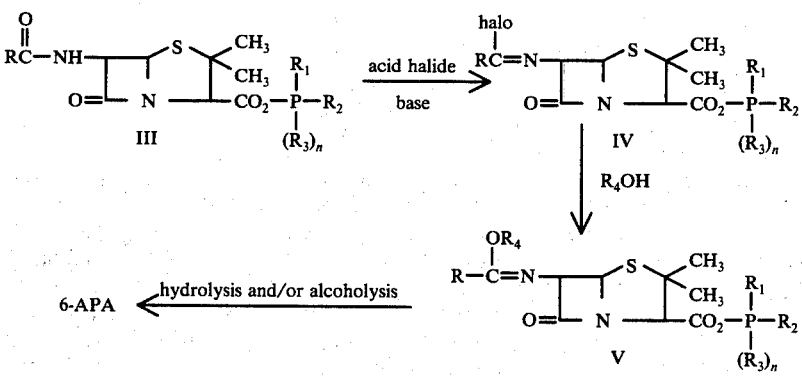

Examples of suitable acid halides are phosphorus pentachloride, phosgene, phosphorus oxychloride, oxalyl chloride, p-toluene sulfonic acid chloride, etc. The preferred acid halides are phosphorus pentachloride and phosphorus oxychloride. The reaction of a compound of formula III with an acid halide is carried out in the presence of acid binding agents such as a tertiary amine base as exemplified by N,N-dimethylaniline, quinoline, pyridine, triethylamine, N-ethylmorpholine, etc.

The reaction of the acid halide with a compound of formula III is carried out at a temperature in the range of −40° to +30° C., depending on the reactivity of the particular acid halide used. A slight excess of acid halide, not more than about 10%, is used in the formation of a compound of formula IV.

The alcohol represented by $R_4OH$ is preferably selected from the group consisting of alkanols having $C_1$ to $C_7$ carbons (e.g. methanol, ethanol, butanol, isobutanol, etc.) and aryl(lower)alkyl alcohols such as benzyl alcohol, 2-phenyl-ethanol, etc. The introduction of the $OR_4$ group on the imino carbon atom is preferably carried out at a temperature of between −40° and −10° C. Once the imino ether of formula V is formed, the imino bond and the protective group on the carboxyl group is split off by hydrolysis or alcoholysis.

The following examples are illustrative of the process of the present invention:

EXAMPLE I

Potassium Penicillin G (60.0 g., 0.161 mole) is stirred in anhydrous methylene chloride (250 ml.), and the mixture is cooled down to −30° C. Dimethylaniline (44 ml., 0.348 mole) is added followed by dropwise addition of phosphorous oxychloride (16.3 ml., 0.178 mole) over 20 minutes at −30° C, and then phosphorus pentachloride (26.2 g., 0.174 mole) is added over two to three minutes at −39 to −35° C. The solution is stirred for 2 hours at −35° C, and butanol (250 ml.) is added as rapidly as possible while keeping the temperature at −30° to −35° C, with acetone-dry ice cooling. The solution is stirred for 3 hours at −35° C and water (225 ml.) is added. The pH is adjusted to 4 at 5° C., by addition of sodium carbonate, and the resulting mixture is seeded with 6-APA and stirred at 0-5° C., overnight. The pH is readjusted to 4 with 35% sodium hydroxide and the mixture is filtered. The cake is washed with 1:1 acetone-water (10 ml.) and acetone (2 × 10 ml.), giving white crystals (3.2 g.). The infrared spectrum is identical with an authentic sample of 6-APA.

EXAMPLE 2

6-APA may be obtained following the procedure of Example 1 using penicillin V in place of penicillin G and using ethyl dichlorophosphite in place of phosphorus oxychloride.

As previously indicated, an excess of a penicillin of formula I may be reacted with a phosphorus halide of formula II to form a poly penicillin-phosphorus anhydride compound. Such compounds would be represented by the formula

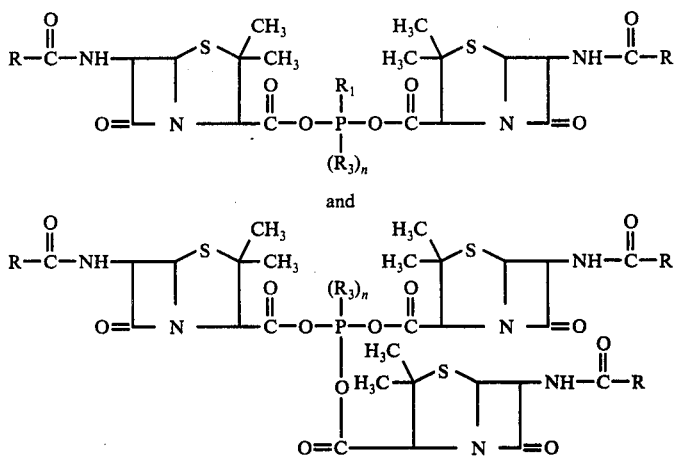

and

These poly penicillin-phosphorus anhydrides are converted to 6-APA following the same reaction scheme illustrated by going from formula III to 6-APA as previously described.

What is claimed is:

1. A process for the preparation of a compound of the formula:

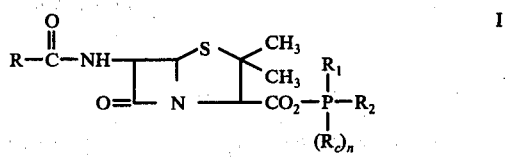

which comprises reacting a compound of the formula:

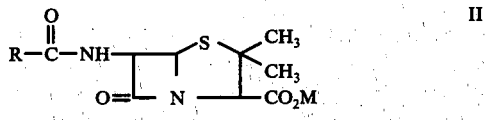

with a phosphorus halide of the formula:

in a molar ratio of about 0.5:1 to 3:1 and at a temperature of between about −40° C and about +10° C; wherein R is selected from the class consisting of benzyl, phenoxymethyl, n-heptyl, 2-pentyl, n-amyl, p-hydroxybenzyl and p-aminobenzyl; M is selected from the class consisting of hydrogen, an alkali metal and a tertiary amine; X is halogen; $R_1$ and $R_2$ are members selected from the class consisting of $C_1$ through $C_7$ (lower)alkoxy, aryl(lower)alkyloxy, aryloxy and halogen; $R_1$ and $R_2$ when joined together are

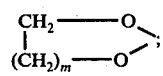

$R_3$ is =O (oxygen); $n$ is either zero or 1; $m$ is a number from 0 through 6, said word aryl meaning phenyl or naphthyl.

2. A process according to claim 1 wherein R is benzyl or phenoxymethyl.

3. A process according to claim 1 wherein said phosphorus halide is selected from the class consisting of phosphorus trichloride, phosphorus oxychloride, diphenyl chlorophosphate, diethyl chlorophosphate, phenyl dichlorophosphate, ethyl dichlorophosphate, ethylene chlorophosphate, diethyl chlorophosphite, ethyl dichlorophosphite, ethylene chlorophosphite.

4. A process according to claim 1 which includes the additional steps of reacting a compound of formula I with an acid halide compound selected from the class consisting of phosphorus pentachloride and phosphorus oxychloride at a temperature between about $-40°$ C to about $+30°$ C. in the presence of a tertiary amine to form the corresponding imino chloride of the formula:

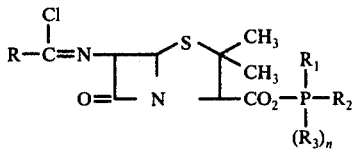

5. A process according to claim 4 wherein said compound of formula III is phosphorus oxychloride and said acid halide compound is phosphorus pentachloride.

* * * * *